United States Patent
Kuo

(10) Patent No.: US 6,735,803 B2
(45) Date of Patent: May 18, 2004

(54) ELECTRICAL DENTIFRICE-DISPENSING TOOTHBRUSH WITH REPLACEABLE BRISTLE UNIT AND REFILLABLE CARTRIDGE

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 134 days.

(21) Appl. No.: 10/159,672

(22) Filed: Jun. 3, 2002

(65) Prior Publication Data

US 2003/0221270 A1 Dec. 4, 2003

(51) Int. Cl.$^7$ ............................................. A46B 13/04
(52) U.S. Cl. ................... 15/22.1; 15/28; 15/29
(58) Field of Search ..................... 15/22.1, 28, 29, 15/110, 167.1, 188; 401/278

(56) References Cited

U.S. PATENT DOCUMENTS

| | | |
|---|---|---|
| 4,326,314 A | 4/1982 | Moret et al. |
| 5,099,536 A | 3/1992 | Hirabayashi |
| 5,321,866 A | 6/1994 | Klupt |
| 5,353,460 A | 10/1994 | Bauman |
| 5,625,916 A | 5/1997 | McDougall |
| 5,784,743 A | 7/1998 | Shek |
| 2003/0077107 A1 * | 4/2003 | Kuo .......................... 401/278 |
| 2003/0084527 A1 * | 5/2003 | Brown et al. ................ 15/22.1 |

FOREIGN PATENT DOCUMENTS

WO   WO 95/08934   * 4/1995

OTHER PUBLICATIONS

U.S patent application Ser. No. 09/649074, Kuo, filed Aug. 28,2000.

* cited by examiner

*Primary Examiner*—Deborah Jones
*Assistant Examiner*—Vivek Koppikar

(57) ABSTRACT

An electrical dentifrice dispensing toothbrush using a replaceable bristle unit with a permanent drive head and handle is described. The replaceable bristle unit consists of a rotary bristle element and a stationary bristle element that has an opening for the flow of dentifrice material through the drive head. The bristle unit is snap-on latched to the side walls of the drive head. Opposing tabs which also function as pressure sensors on the bristle unit are pressed toward each other to release the bristle unit. A linkage is used to convert the rotation of the drive shaft to a planar oscillation that enables a compact drive head configuration. The dentifrice dispensing is accomplished by using a rotary solenoid for actuating an internal button that applies pumping pressure to the dentifrice material. As a benefit to arthritis suffers, no external squeezing action is involved.

18 Claims, 11 Drawing Sheets

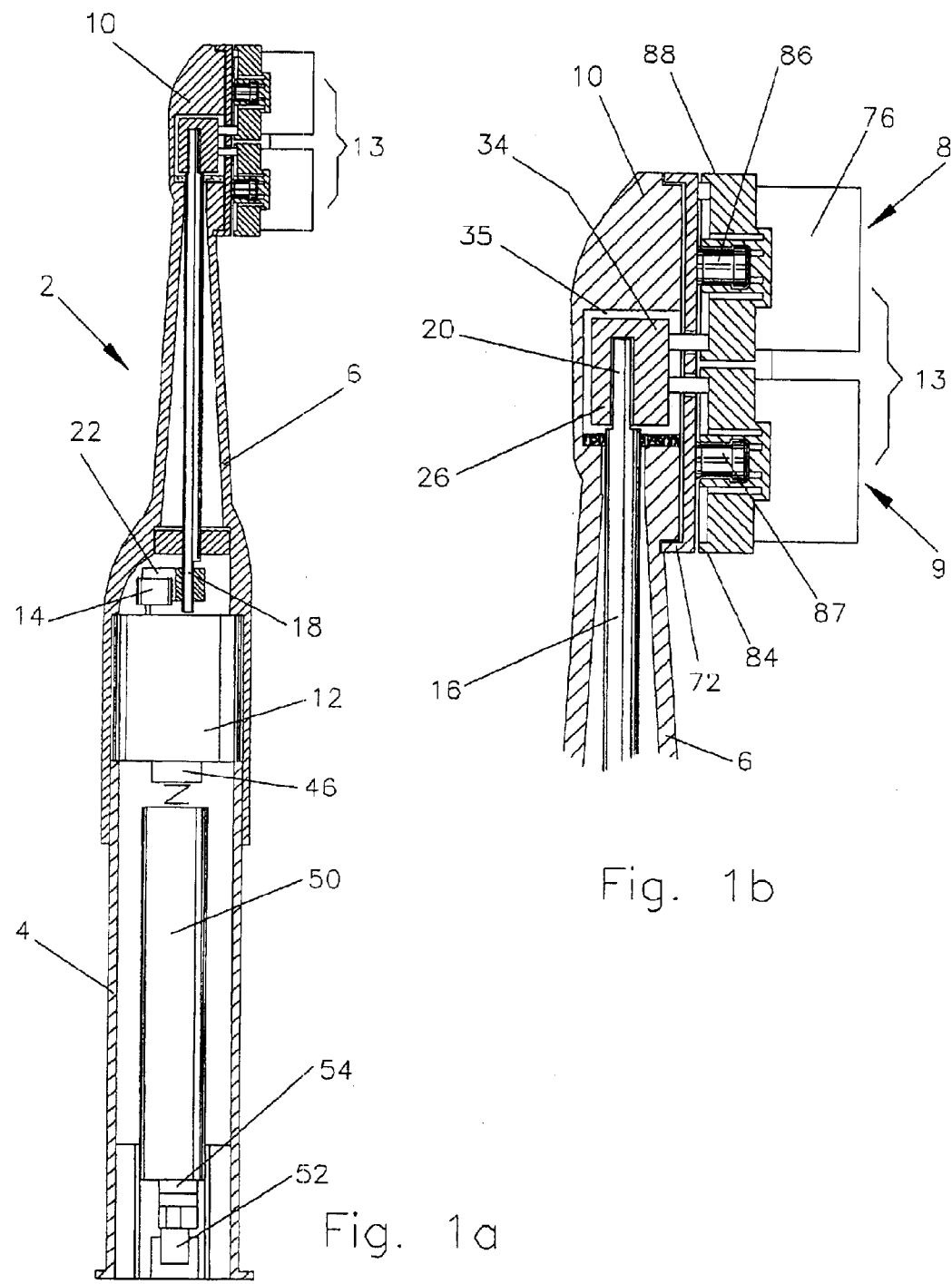

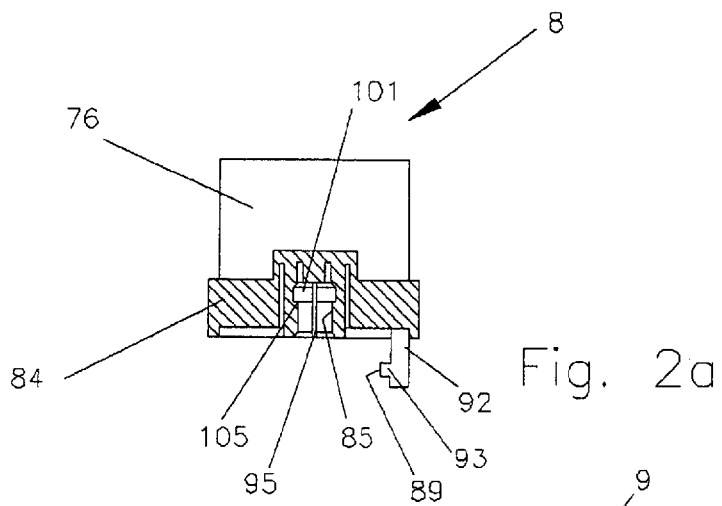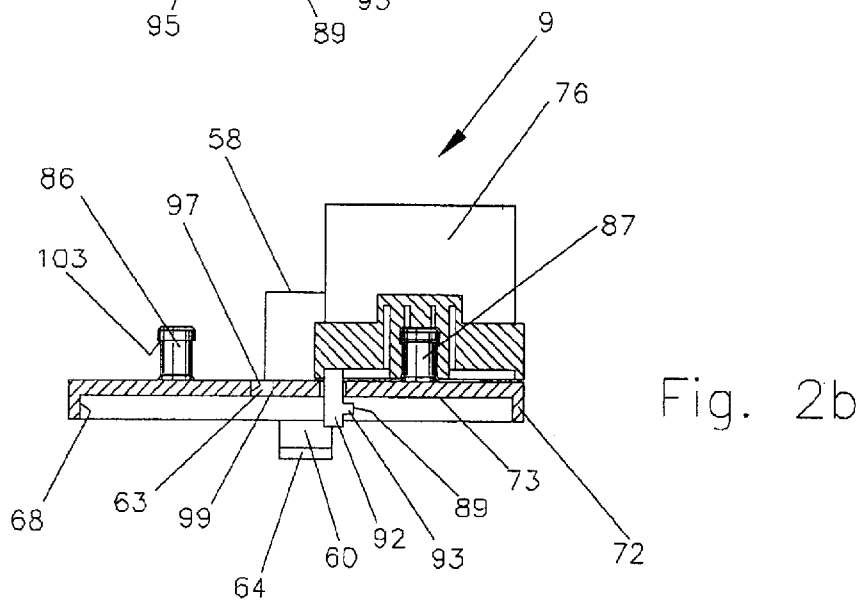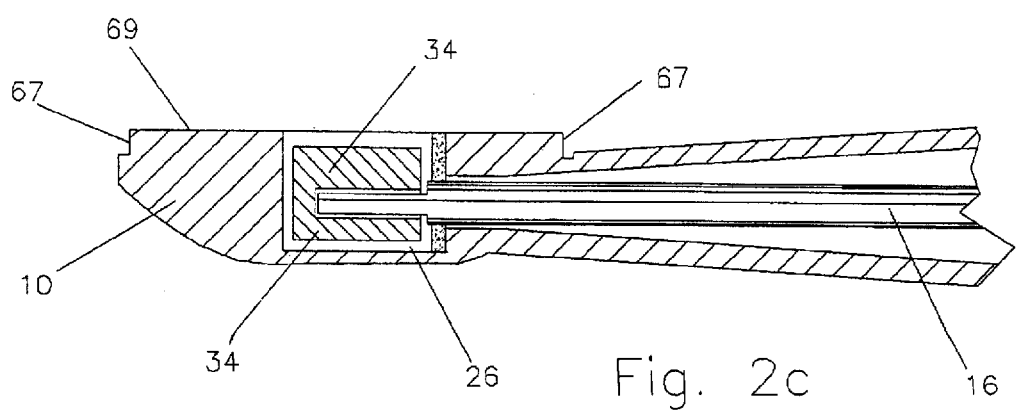

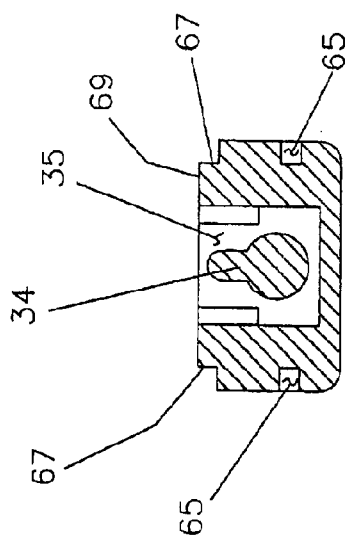
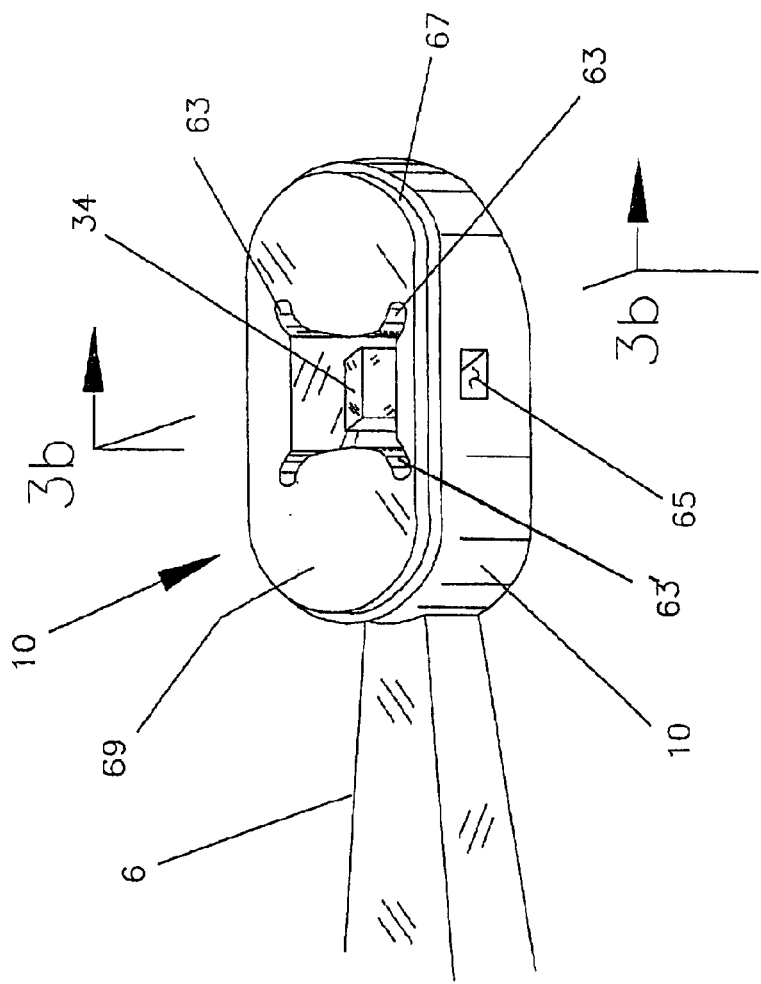
Fig. 3b
Fig. 3a

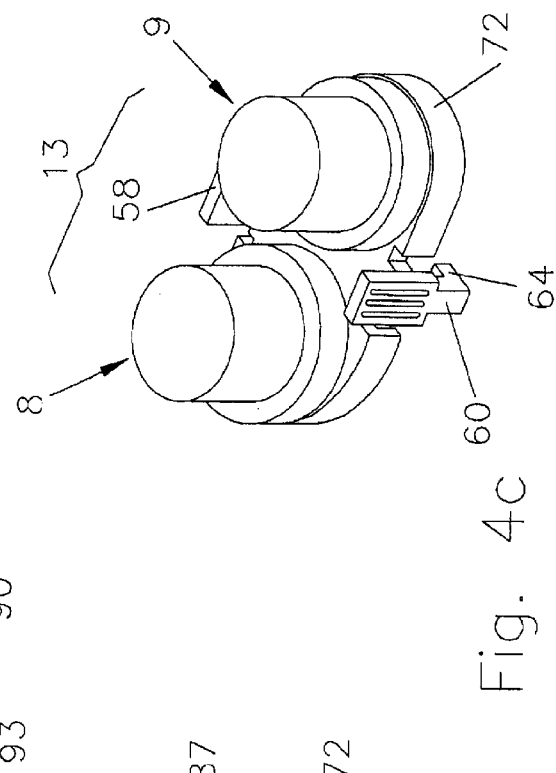
Fig. 4a
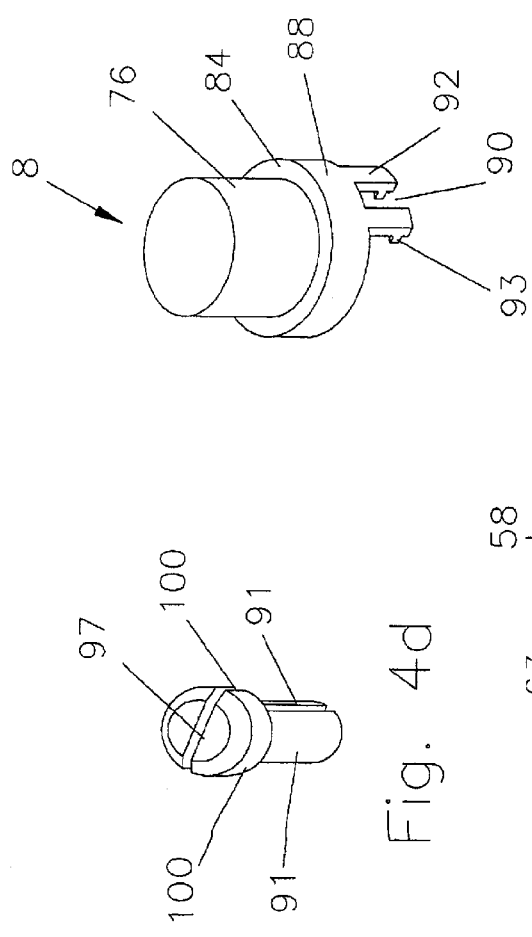
Fig. 4d
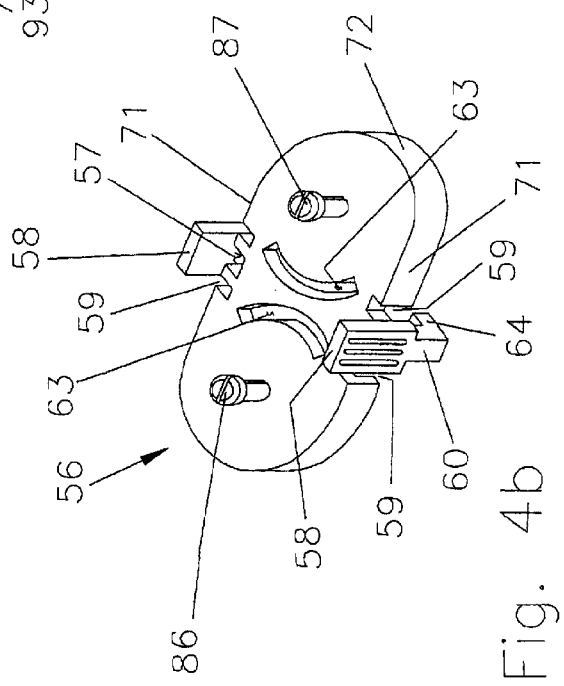
Fig. 4b
Fig. 4c

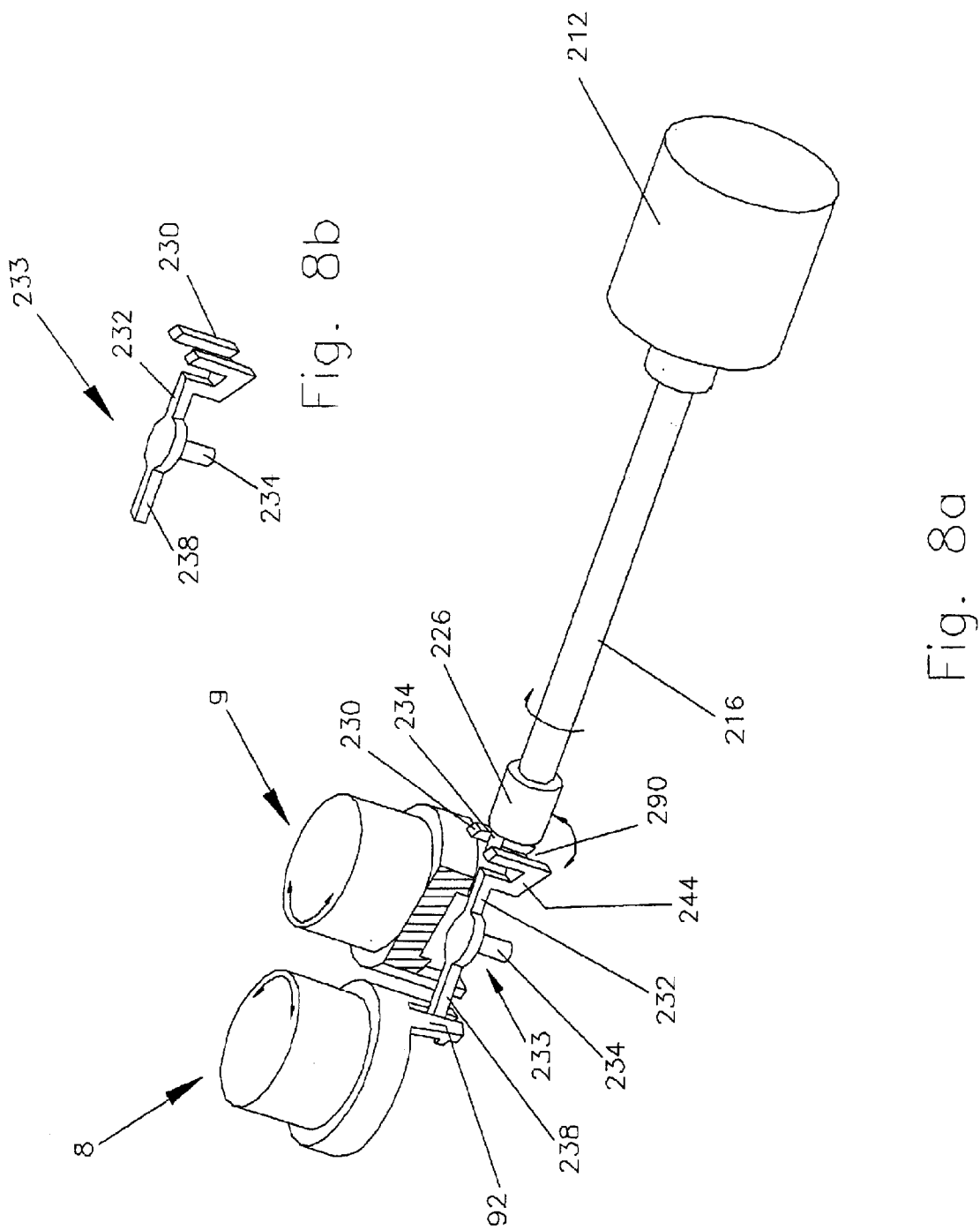

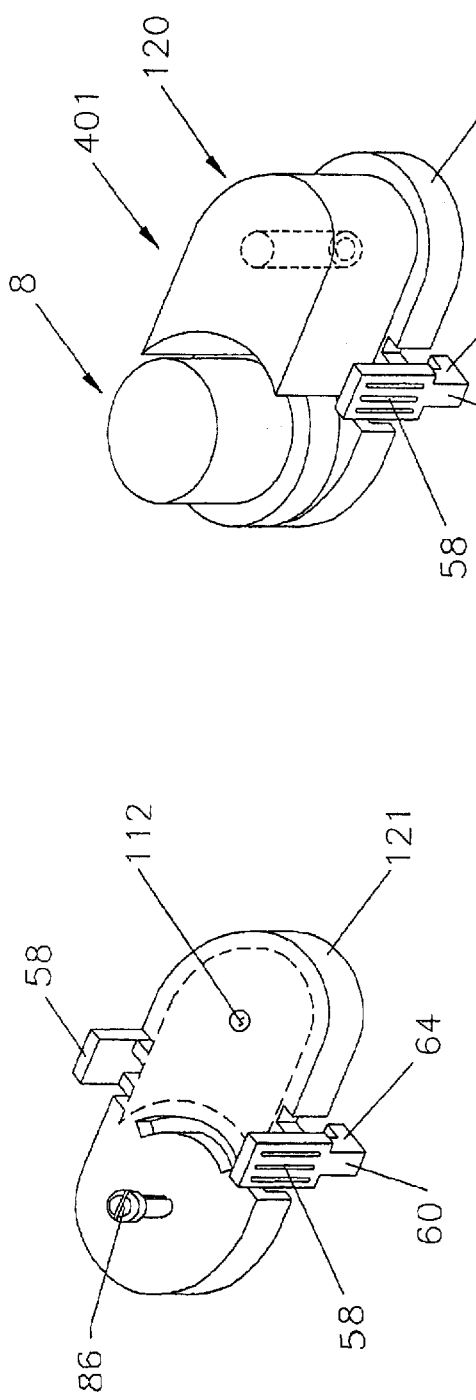
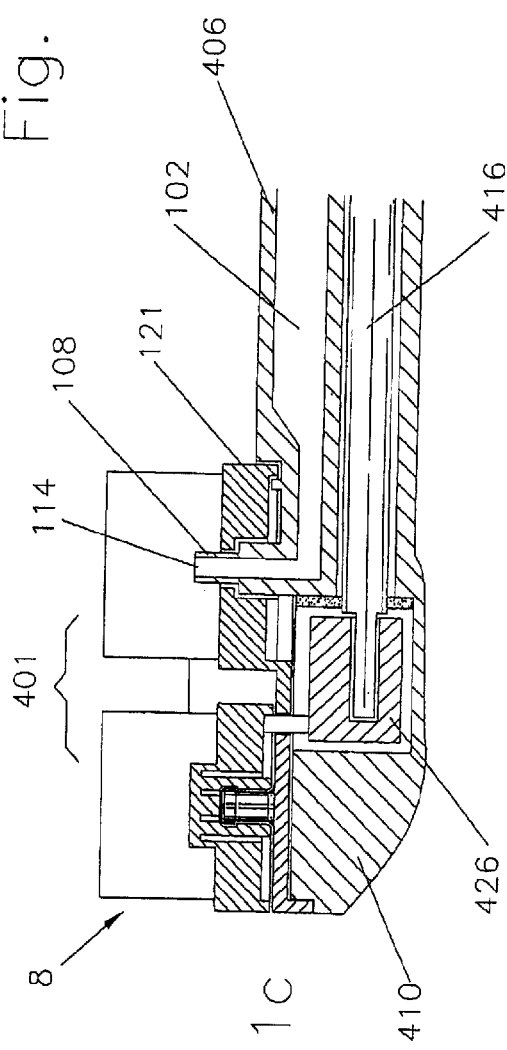
Fig. 11a
Fig. 11b
Fig. 11c

ELECTRICAL DENTIFRICE-DISPENSING TOOTHBRUSH WITH REPLACEABLE BRISTLE UNIT AND REFILLABLE CARTRIDGE

BACKGROUND OF THE INVENTION

It has been recognized that an electrical toothbrush is more effective in removing plaque and preventing gum disease than a conventional manual toothbrush. It is also well known that the manual squeezing action of dentifrice dispensing presents a significant challenge to severe arthritis suffers who lack finger dexterity and strength. Thus a total-electrical toothbrush is desirable for everyday dental care and a necessity for the physically challenged. Oral hygiene requires that toothbrush bristles should be replaced on a regular basis for maintaining bristle effectiveness and minimizing bacteria buildup. While the entire toothbrush can be replaced, it is desirable to discard only the part having bristles and retain the drive mechanism and the brush handle as permanent parts for minimizing the replacement costs. For long service life of the permanent parts, all wearable parts need to be included in one replacement unit. For the ease of replacement, it is desirable to have a replaceable snap-on bristle unit for fastening on a permanent drive head containing driving components. For the convenience of portability, it is desirable to have a self-contained, dentifrice dispensing electrical toothbrush for brushing anywhere at anytime. For the ease of operation especially for the physically challenged, it is desirable simply to press on an electrical switch for the automatic dispensing of dentifrice material to the top of the bristles. The objects of this invention are to achieve all of the above desirable features in one electrical toothbrush.

(1) Field of the Invention

The present invention relates to electrical dentifrice dispensing toothbrushes with a replaceable bristle unit.

(2) Prior Art

It is recognized in the prior art that electrical toothbrushes which have oscillatory brush elements are more effective than toothbrushes with rotating brush heads. The reciprocating movement and wiping action of the bristles provides an effective means for plaque removal. U.S. Pat. No. 4,326,314 by Moret and Jousson describes a means for oscillating a brush head through an oscillating shaft which is connected to a cam riding on a biased wheel mounted on the shaft of a motor. Since the source of vibration is at the cam and the motor which is usually located in the handle, a strong vibration may cause discomfort during brushing.

To minimize the vibration at the handle, U.S. Pat. No. 5,625,916 by McDougall provides a means for converting rotary motion to oscillatory motion near the brush head area which is remote to the motor. It uses a bent remote-most end of a shaft having rotary motion to engage with a slot formed on the side of a bristle holder to force it to oscillate back and forth as the bent remote-most end is driven in a circular annular path. While it achieves relocation of the vibration source to the brush head, the central axis of the bent remote-most end is required to intersect with the central axis of the brush head. This requirement precludes its application from simultaneously driving two brush heads since the same central axis of the remote-most end of a shaft cannot intersect two separate central axes in its circling positions. Also, its use of a closed ended slot on the side of the brush head for engagement also prevents the remote-most end from reaching more than one brush head.

Owing to its complex assembly, the entire neck including the brush head, the mounting base and the drive shaft assembly are replaced when the brush head is changed.

U.S. Pat. No. 5,784,743 by Shek uses an off-set finger mounted at the end of a rotating shaft for engaging the fork of a pivotally supported wobble plate which is meshed with a gear for oscillating a brush head. The use of the closed end fork and the blocking of the extension of the finger by the pivoting and gear-meshing mechanism prohibit its application to oscillate two brush heads. Similarly, the replacement of the whole neck including the drive shaft is required when the brush head is replaced.

The prior art has also recognized that the brushing area is broadened and the brushing time reduced when two brush heads are used instead of one. For oscillating two brush heads, U.S. Pat. No. 5,353,460 by Bauman uses an oscillating shaft to drive one brush head and utilizes a linkage between the two brush heads to drive the other brush head. The linkage requires a pivoting post on each brush head which adds an increased friction load to the drive mechanism for oscillation of the brush heads. U.S. Pat. No. 5,099,536 by Hirabayashi uses two shafts aligned at different angles. The gearing mechanism allows for driving more than one brush head but its drive mechanism does not cause oscillatory motion. In order to change the brush head, each of the above two patents also requires replacing the neck connected to the brush head which includes part of a drive shaft assembly.

A description of an electrical toothbrush which dispenses liquid is provided in U.S. Pat. No. 5,321,866 by Klupt. The patent discloses a delivery means for a cleaning liquid through oscillating brush heads. A motor is connected to a series of gear mechanisms causing a drive shaft to oscillate and a piston to pump the liquid through a flow conduit to openings in the brush head. Because it is connected to the same motor, the motorized piston pumps the liquid continuously while the brush heads are oscillating. This common drive mechanism is not desirable for dispensing material that only needs to be dispensed prior to the brushing action.

A dentifrice dispensing electric toothbrush of U.S. patent application Ser. No. 09/649,074 by Kuo mounts a pair of rotary bristle elements on a pair of posts attached to a brush head and uses a retention cradle for keeping the two rotary bristle elements in free-to-rotate positions. The neck of the toothbrush includes a channel which is part of the flow path for dentifrice material that is pumped from the cartridge to the brush head. The pumping is achieved by using an elastic compressible button positioned on the external surface of the brush handle for manually supplying a pumping force to pump dentifrice and for simultaneously activating a switch positioned inside the brush handle to energize the motor. Although only the bristle elements and the retention cradle are replaced, the posts which are subject to wear from the oscillation motion remain on the brush head. A worn post can cause wobbling of oscillating bristle element and noise that results in reduced service life of the toothbrush. Also, catch arms used in the retention cradle are only for keeping the bristle elements in place in packaging, not required in the operation of the toothbrush. Furthermore, the elevated position of the cradle platform from the bristle base is a barrier for the free brushing motion and running of cleaning water. As for dentifrice dispensing, the requirement of manual squeezing on the compressible button on the handle is a major hindrance for a severe arthritis suffers who lack of finger dexterity and strength.

In view of the deficiencies as exemplified in above patents in the prior art, there is a pressing need for an electrical dentifrice dispensing toothbrush that can provide permanent drive head and handle with minimal replacement of bristle parts, and a pumping means that does not require manual squeezing action for dispensing the dentifrice material.

SUMMARY OF THE INVENTION

This invention provides an electrical toothbrush that satisfies the needs for less throw-away, easy replacement of bristle elements and high cleaning efficiency. It also provides an electrical means of dispensing dentifrice material from a cartridge attached to the brush head for the convenience of users in general and especially for severe arthritis sufferers who have difficulty in the manual squeezing action of dispensing toothpaste. The replaceable bristle unit which is mounted on a permanent drive head consists of a rotary bristle element, a staionary bristle element, and a detachable snap-on platform which has a post for supporting the free-rotation of the rotary bristle element. The mounting of the rotary bristle element on the post is un-detachable as detachment is prevented by the engagement of the annular groove in the bushing of the bristle element and the protruding rim of the post with 90 degree detent angle. All the wearable parts are included in the replaceable bristle unit and the driver components, including the drive shaft, remain in the permanent drive head and the body of the electrical toothbrush. The replaceable bristle unit is locked to the drive head through the engagement of its latch arms with the latch recesses on the side walls of the drive head. The latch arms are released for replacing the bristle unit by applying an opposing force on the tabs that are on the opposite ends of the latch arms which are hinged on the edges of the detachable platform. The tabs are optionally layered with rubber material and positioned below the bristle surface and for protecting gums from excessive brushing pressure. The replaceable bristle unit of present invention may have two rotary bristle elements or a combination of a rotary and a stationary bristle element. For achieving the use of the minimal disposal bristle unit with a compact drive head, the present invention optionally employs an oscillation conversion linkage for converting the rotational motion of a drive shaft at the input end to a planar oscillation in the output end for driving the rotary bristle element. The planar oscillation motion reduces the height requirement (in the bristle direction) for the drive head.

The present invention also includes an electrical dentifrice dispensing toothbrush which uses a replaceable bristle unit and an electrical means of delivering dentifrice material from a cartridge in the handle to the top of bristles. To achieve these functions, the detachable platform of the replaceable bristle unit has an opening for slidably mounted on the wall of a spout opening extending from the top of the drive head. The delivery of the dentifrice material is achieved by using a toothbrush neck having two separated channels. One channel houses the drive shaft and the other channel functions as part of the flow path for the dentifrice material as it is pumped from the handle to the brush head. The electrical pumping mechanism includes a switch, a rotary solenoid, and a plunger in contact with a resilient compressible button. The activation of the switch causes the rotary solenoid to move the plunger to press on the resilient compressible button for applying pressure to force dentifrice material to flow to the top of the bristles. Through a control mechanism, release of the switch causes the rotary solenoid, the plunger, and the elastic button back to their original home positions and accordingly the follower inside the cartridge advances to keep the dentifrice material inside the cartridge at a packed condition for next pumping action.

The replaceable bristle unit of present invention is applicable to dual rotary bristle elements, a combination of rotary and stationary bristle elements, or a combination of rotary and dentifrice dispensing bristle elements.

The essential components of the electrical toothbrush include 1) a handle which serves as a housing for a motor, batteries and a cartridge containing dentifrice material; 2) a replaceable bristle unit having a rotary bristle element with a drive notch and a detachable platform having latch arms; 3) a drive head having a driver component that engages with the drive notch of the bristle element and latch recesses on its side walls for locking with the latch arms of the detachable platform; 4) a neck which connects the handle and the drive head; 5) a drive mechanism that is driven by a motor and imparts an oscillatory motion to the driver component in the drive head. The electrical dentifrice dispensing toothbrush also includes; 6) a series of flow path components including a spout in the drive head, a flow channel in the neck, a pump chamber, a one-way valve and an internal resilient compressible button; 7) an electrical actuation mechanism including a switch, a rotary solenoid, and a plunger which presses on the resilient compressible button for dispensing the dentifrice material when the switch is actuated; 8) a refillable dentifrice cartridge.

BRIEF DESCRIPTION OF THE DRAWINGS

FIG. 1a is a cross section view of a drive mechanism for an electrical toothbrush having a replaceable bristle unit.

FIG. 1b is an enlarged cross section side view of the drive mechanism; and the replaceable bristle unit shown in FIG. 1a.

FIG. 2a is a cross section side view of an oscillatory bristle element.

FIG. 2b is a cross section side view of a snap-on bristle platform.

FIG. 2c is a cross section side view of a drive head.

FIG. 3a is a perspective view of a drive head.

FIG. 3b is a cross section view along 3b—3b of the drive head shown in FIG. 3a.

FIG. 4a is a perspective view of an oscillatory bristle element.

FIG. 4b is a perspective view of a snap-on bristle platform having two posts.

FIG. 4c is a perspective view of a replaceable bristle unit with two oscillatory bristle elements.

FIG. 4d is a perspective view of a post.

FIG. 8a is an illustration of the engagement between a drive shaft, bristle elements and an oscillation linkage shown in FIG. 7c.

FIG. 8b is a perspective view of the oscillation linkage shown in FIG. 8a.

FIG. 9b is an illustration of the engagement between a drive shaft and the oscillation linkage shown in FIG. 9a.

FIG. 11a is a perspective view of a snap-on bristle platform having a post and a through hole located in an array of bristle planting holes.

FIG. 11b is a perspective view of a replaceable bristle unit having an oscillatory bristle element and an array of stationary bristles with a dentifrice conduit therein.

FIG. 11c is an enlarged cross-section view of the mounting of the replaceable bristle unit as shown in FIG. 11b on a drive head having a flow conduit as shown in FIGS. 10a and 10b.

DETAILED DESCRIPTION OF PREFERRED EMBODIMENTS

Figure 5B:
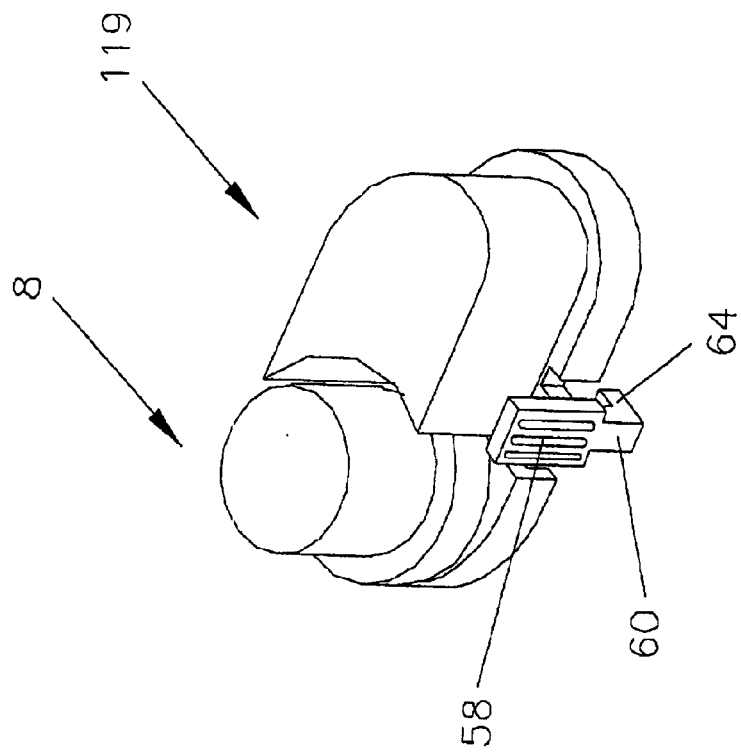
FIG. 5b is a perspective view of a replaceable bristle unit having an oscillatory bristle element and an array of stationary bristles.

FIG. 1a shows an electrical toothbrush 2 having a handle 4 and a drive head 10 connected by neck 6. Replaceable bristle unit 13 having bristle elements 8 and 9 detachably mounted on drivehead 10. Motor 12 and batteries 50 are positioned within handle 4. Leaf spring contact 54 is situated at the end of battery 50 and switch 52 extends through an opening in the base of the handle. Batteries 50 are connected to motor 12 by contact 46. Drive shaft 16, having a central longitudinal axis with first end and second end, is positioned in neck 6. Drive shaft 16 and motor 12 are connected by an U-Shaped cam assembly 22, which imparts an oscillating motion to the drive shaft through the engagement of its first end 18 with bias wheel 14 mounted on motor 12. Mounted on second end 20 of the drive shaft is an oscillation driver which is drive tab 34 on the base of cap 26 having a recess for the mounting. Drive tab 34 extends radially outward from the central longitudinal axis of drive shaft 16 and oscillates within a limited angle in concert with drive shaft 16. As explained below, drive tab 34 in turn imparts its oscillating motion to bristle elements 8 and 9 which increases brushing efficiency. The principle operation of an oscillatory electrical toothbrush is known in the prior art and a detailed description of the drive mechanism as shown in FIG. 1a is given in the patent application Ser. No. 09/649,074 by Kuo.

As shown in FIG. 1b, FIG. 2a and FIG. 4a, a plurality of bristles 76 are attached to the top surface of base 84 of first bristle element 8. Notch wall 92 with drive notch 90 is appended to side wall 88 of bristle base 84. The underside of bristle base 84 has split bushing walls 85 which are shaped to mate with first post 86 of platform 72. When mounted, notch walls 92 are positioned and extended beyond first slot 63. First slot 63 is of segmented circular annular shape with inner edge 97, shown in FIG. 2b, having equal radial distance from the central axis of first post 86. Drive notches 90 of first and second bristle elements 8 and 9 accommodates drive tab 34 such that when drive tab 34 is positioned in drive notch 90, the oscillating motion of drive tab 34 causes first and second bristle elements 8 and 9 to freely oscillate on first and second posts 86 and 87 respectively. Advantages of having a pair, of matching bushing and post in, one replaceable bristle unit are that both bushing and post are wearable and undergoing the same dimensional variation under the same usage environment and duration. Replacing the bristle element and the detachable platform with the post at the same time avoids possible dimensional mismatch which may occur when replacing with a new rotary bristle element on a used post. The following provides more detailed descriptions of the structures and functions of an electrical toothbrush of the present invention.

A replaceable bristle unit 13 is comprising first and second bristle elements 8 and 9 and platform 72. Platform 72 is attachable to and detachable from drive head 10 (shown in FIGS. 3a and 3b), which permits the removal and replacement of bristle elements 8 and 9. A, pair of opposing tabs 58 extend from the top surface of platform 72. Portions of tab 58 overlap portions of arms 60 and are configured in a manner such that inward deflection of tabs 58 toward each other causes outward deflection of opposing arms 60 and their disengagement from drive head 10.

FIGS. 2a, 2b and FIG. 4d show the mounting of first and second rotary bristle elements 8 and 9 on first and second posts 86 and 89 respectively. The one-way engagement of bristle base 84 of bristle element 8 on post 86 is enabled by the mounting of two half-circle-shaped split bushing walls 85 on the underside of bristle base 84 on two half-circle-shaped split shaft walls 91 (FIG. 4d) of post 86. Gap 95 between the split walls 85 allows wall deflection apart from each other while gap 97 of post 86 allows for deflection of its split walls 91 toward each other. Each bushing-wall 85 is of cantilever configuration extending from the underside of bristle base that provides flexibility for outward deflection for accommodating the insertion of the post. On the other hand, each split shaft-wall 91 of post 86 is also of cantilever configuration extending from the platform 72 that enable further ease of insertion inside the bushing walls 85. For preventing disengagement, first post 86 has retention rim 100 on each split shaft wall and the flexible bushing has annular groove 101 (FIG. 2a) on each split bushing wall at corresponding mating positions. The diameter of retention rim 100 of post 86 is smaller than the diameter of annular groove 101 engaged therein but is larger than the inner diameter of bushing walls 85. Also, the nominal inside diameter of bushing walls 85 is slightly larger than the diameter of post 86 for establishing a clearance between the post and the bushing for the free rotation of the bristle element. Besides, both the underside lower edge 103 (FIG. 2b) of retention rim and the corresponding edge 105 (FIG. 2a) of the annular groove are right-angle (90 degree) with respect to their rotational axis. This configuration prevents bristle base dislodged from the post. The beveled surfaces at the free end of flexible busing wall is for facilitating the insertion of the beveled top surface of the post. The engagement dimensions including lengths, diameters and wall gaps of the mating pair of a bushing and a post are designed for enabling free rotation, ease of mounting and preventing dislodgment of the bristle element. The orientation of the gap 95 (FIG. 2a) between the two split walls of the bushing is at right-angle (90 degree) with respect to the symmetry plane (crossing the axis of the bushing) of notch walls 92, while the orientation of gap 97 between two split walls of the post is aligned with the symmetric plane (crossing the post) of the drive head. As the maximum oscillation angle of notch walls is less than 90 degree from the symmetric plane of the snap-on platform, the oscillation motion of the bushing walls 85 does not cause its split gap 95 to overlap with the split gap 97 of post 86. The smoothness of oscillation motion of bristle base 84, therefore, is not affected by the presence of two gaps 95 and 97. Furthermore, for enhancing the retention of the bristle element when oscillating, rib 93 is added to a notch wall's inner surface facing the central axis of the bushing. The radial distance of outer surface of a notch wall 92 from the central axis of bushing is smaller than the radial distance of outer edge 99 of first slot 63 from first post 86. But the radial distance of inner edge 89 of rib 93 is smaller than that of inner edge 97 of first slot 63 such that rib 93 has an interference with inner edge 97 of slot 63 when first bristle element 8 is fully mounted on post 86. However, in the mounting of first bristle element, the flexibility of the bushing walls 85 allows deflections of the bushing walls against first post 86 and slight tilting of the bristle element for inserting notch walls 92 in a slanted orientation to slide into slot 63 and then upright itself in mounting on the post with the central axis of bushing walls 85 coincide with that of first post 86. The height of rib 93 with respect to bottom surface 73 of platform 72 when rib 93 is at the mounted position is determined in a manner that the clearance between rib 93 and bottom surface 73 of platform 72 enables free oscillation of bristle element 9. The two interference features as described, e.g. between rib edge 89 and slot edge 97, and between post rim 100 and bushing groove 101, provides an effective retention means to ensure sufficient retention force for preventing the detachment of a bristle element from the post being mounted at high speed oscillation. During brushing, the brushing pressure pushes the bristle element against the post, therefore, the bristle element cannot detach from the post under the brushing condition. Alternatively, a retention means can be the engagement between ribs attached at the end of bushing walls and annular grooves created on shaft walls of a post.

Moreover, when bristle element 9 is latched in position, a clearance between the top surface of the platform 72 and the bottom surface of the bristle element allows for the free oscillation of the bristle element on post 87. In manufacturing, because of the small protrusions of retention rims 100 from the post walls and the shallow annular recess 101 of the bushing walls as well as the flexibility of cantilever structures, these undercut features can be injection molded. The detachable platform and the two mounted bristle elements forms a replaceable bristle unit for locking on the drive head. Further referring to FIGS. 4b and 4c, for integrating the locking feature to the detachable platform, two notches 59 are provided on each side of two opposing latch arms 60 which are positioned at the middle of each opposing edge 71 of platform 72 for enabling the deflection of the latch arms 60. In addition to adding flexibility of the latch arms 60, through hole 57 positioned next to the inner edge of each latch arm is for the creation of the inward retention rib 64 at the end of latch arm 60 by the injection molding process.

For mounting of a replaceable bristle unit, the, drive head of the present invention as shown in FIGS. 3a, 3b consists of the drive head base having side walls including latch recesses 65, a top 69 having periphery edge 67 and oscillation first and second slots 63 and 63' which are for accommodating notch walls 92 of rotary bristle elements 8 and 9 respectively. Drive tab 34 situated in recess 35 is in communication with the drive motor contained in the handle of the electrical toothbrush. Referring to FIGS. 2b, 2c, peripheral inner rim surface 68 on the underside (bottom) of snap-on platform 72 matches with the corresponding peripheral edge surface 67 of the top 69.

The platform features as described for the mounting of two rotary bristle elements in FIGS. 4a, 4b, 4c and 4d are applicable to a replaceable bristle unit having a rotary bristle element and a stationary bristle element. FIG. 5a shows a detachable platform having split post 86 and oscillation slot 63 for the mounting of bristle element 8, bristle area 117 having an array of molded-in tuft holes (not shown) for implanting bristles of stationary bristle element 119 and latch arms 60 for latching to the drive head of an electrical toothbrush. The detachable platform also has a rim wall as a locating feature for snug fitting on the peripheral edge of the drive head, which is similar to the detachable platform of the dual rotary bristle elements as described previously.

Figure 6C:
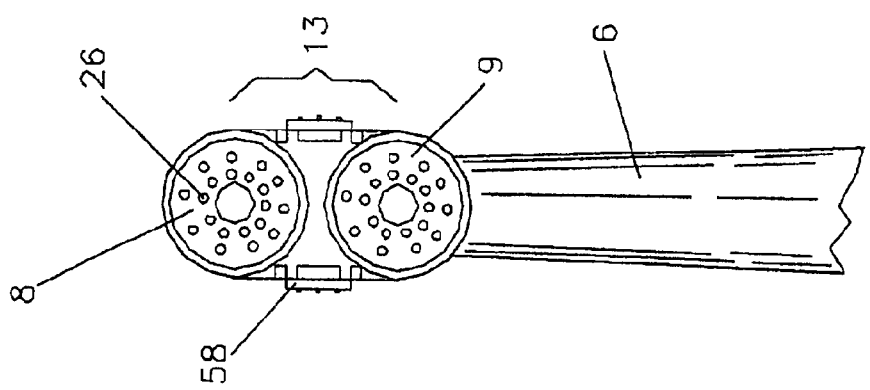
FIG. 6c is a top view of the replaceable bristle unit having notches and openings on the opposing edges of the detachable platform.
Figure 6B:
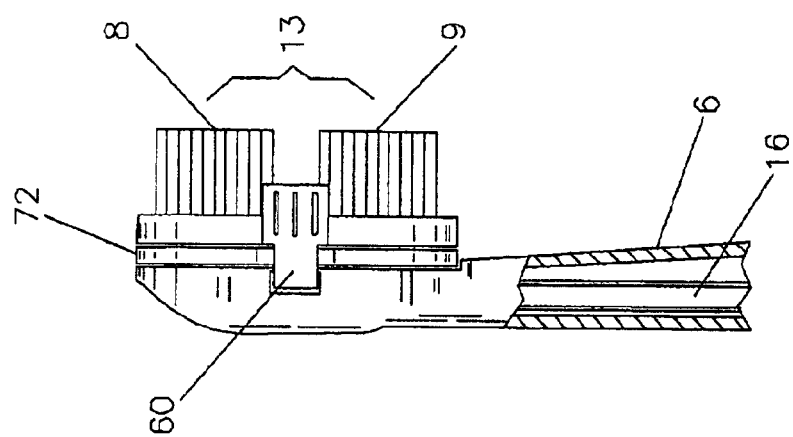
FIG. 6b is a side view of the mounting of a replaceable bristle unit having latch arms locked on the drive head.
Figure 6A:
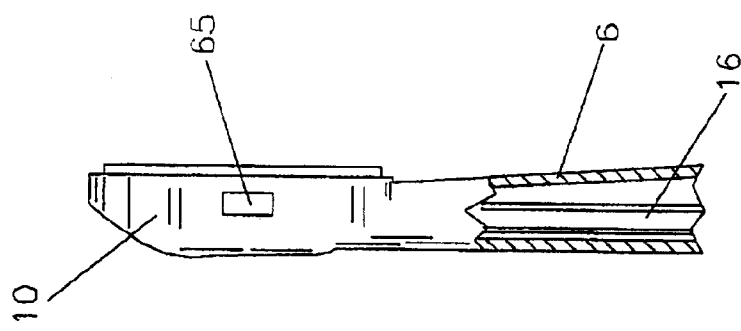
FIG. 6a is a side view of a drive head showing a latch recess on a side wall.

FIGS. 6a, 6b and 6c show external views of the mounting of replaceable bristle unit 13 on a drive head 10. Latch recess 65 on side wall of drive head 10 as shown in FIG. 6a is mated with rib 64 (shown in FIG. 4b) at bottom end of latch arm 60 of detachable platform 72 of replaceable bristle unit 13 which has dual rotary bristle elements 8 and 9 as shown in FIG. 6b. The width, thickness, depth, and position of inward extending ribs 64 are designed for mating with the corresponding dimensions of latch recesses 65 on each side of drive head 10 with tight tolerances for secure engagement. Furthermore, the height of each opposing tabs 58 is designed for making tabs 58 as pressure sensors by which a user reduces the brushing pressure when a tab touches teeth or gum during brushing and that the tabs are coated with rubber layers for cushioning and protecting gums. FIG. 6c shows the top view of the mounting of replaceable bristle unit 13 on drive head 10.

Figure 7A:
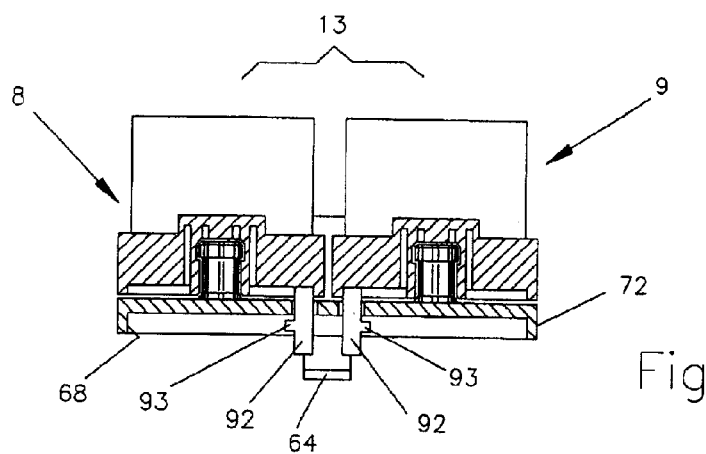
FIG. 7a is a cross-section view of a replaceable bristle unit.
Figure 7B:
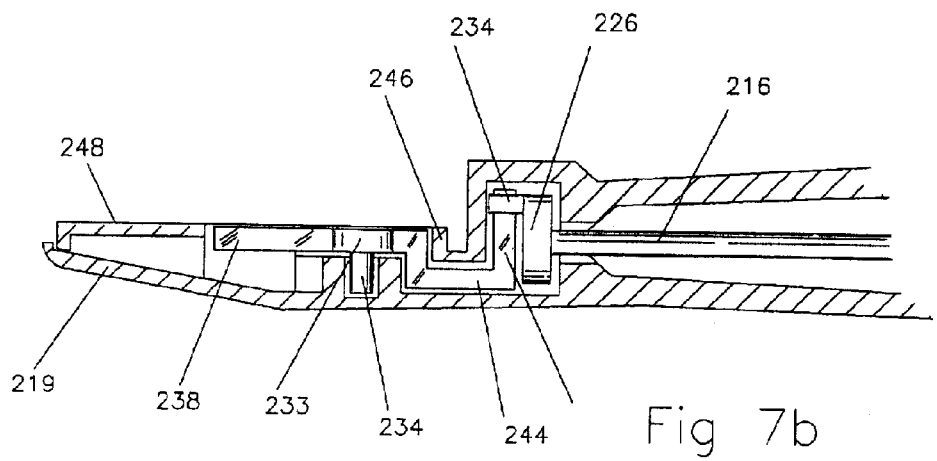
FIG. 7b is a cross section view of a drive head having an oscillation linkage with an elbow-shaped lever.
Figure 7C:
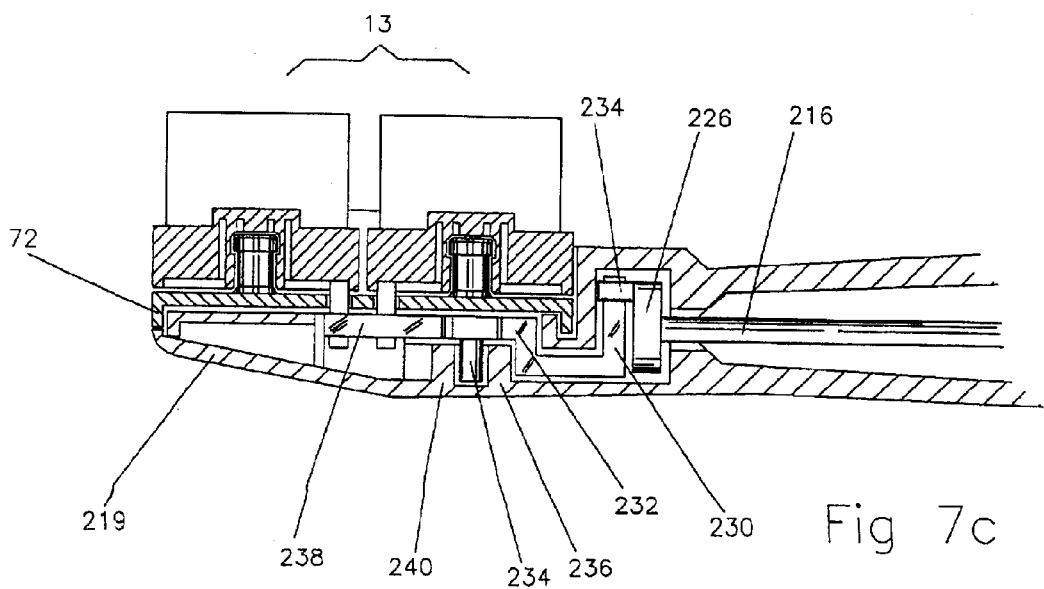
FIG. 7c is a cross section view of the mounting of a replaceable bristle unit on a drive head.

FIGS. 7a, 7b and 7c show a low-profile compact drive head of present invention for mounting replaceable bristle unit 13 having two rotary bristle elements 8 and 9. The oscillation driver of low-profile drive head 219 is an oscillatory conversion linkage 233 for converting circular cam-motion at input end of the linkage to a planar oscillating motion at the output end. As shown in FIGS. 8a and 8b oscillation conversion linkage 233 consists of a pair of notch walls 230 at the input end, a swing arm 238 at the output end, and a stud shaft 234 extending from linkage lever 232 that connects the input end and the output end. Stud shaft 234, which is supported by bushing 236 as shown in FIG. 7c attached to drive head base 240, functions as a pivot point for the oscillation of linkage 233. Drive notch 290 formed between two parallel notch walls 230 at input end 230 is engaged with offset rod 234 of cam 226 mounted on the second end of the drive shaft 216, which is directly coupled to motor 212 in a manner such that the central longitudinal axis of offset rod 234 is parallel to and offset from the central longitudinal axis of drive shaft 216.

Rotation of drive shaft 216 and cam 226 cause movement of offset rod 234 in drive notch 290 in a manner that it imparts an oscillating motion to lever 232 against stud shaft 234, which is inserted in bushing 236 on the inner surface of bottom wall 240 of drive head base 219. Lever 232 and stud shaft 234 transmits the rotational motion of the drive shaft 216 into planar oscillating motion of swing arm 238 in a plane parallel to that of platform 72. Through the engagement with the notches of the two bristle elements 8 and 9 which face each other, swing arm 238 transmits the oscillation motion to bristle elements. The use of the planar oscillating motion as input for driving the oscillation of the bristle elements reduces the functional height (in the axial direction of stud shaft) required for the drive head as compared to the non-planar oscillation of drive tab 34 used in FIG. 1a. It also enables the use of parallel contact surfaces for the swing arm in the areas engaging with the notch walls of the bristle element for reducing the contact pressure, therefore, prolongs the service life of the linkage lever. Besides, the planar oscillation does not exert lifting force on the notch walls that tends to separate a rotary bristle element from a post.

Furthermore, structurally the length of notch walls 230 is sufficient to enable the inner surface of the notch wall to remain in contact with the offset rod 234 during a full 360 degree rotation of drive shaft 216. The width of notches 290 is the same as the diameter of offset rod 234. The inner surfaces of the notches are rounded to reduce friction and minimize the clearance between the offset rod and the drive notches. In addition, linkage lever 232 on the input end is of elbow shape configuration 244 enabling the creation of rim wall 246 on the top 248 of drive head 219 for snug fitting with the inner surface of rim wall 68 of platform 72 which supports two rotary bristle element 8 and 9. In manufacturing, the oscillation conversion linkage may be injection molded either of high strength and wear-resistant plastic material or of metal, in which all corners are rounded. Besides, rim wall 246 provides peripheral structure support and sealing surface similar to the function of edge surface 67 as illustrated in FIG. 3a. When the bristle unit is detached, the recess area of the drive head is exposed for cleaning if needed.

Figure 5A:
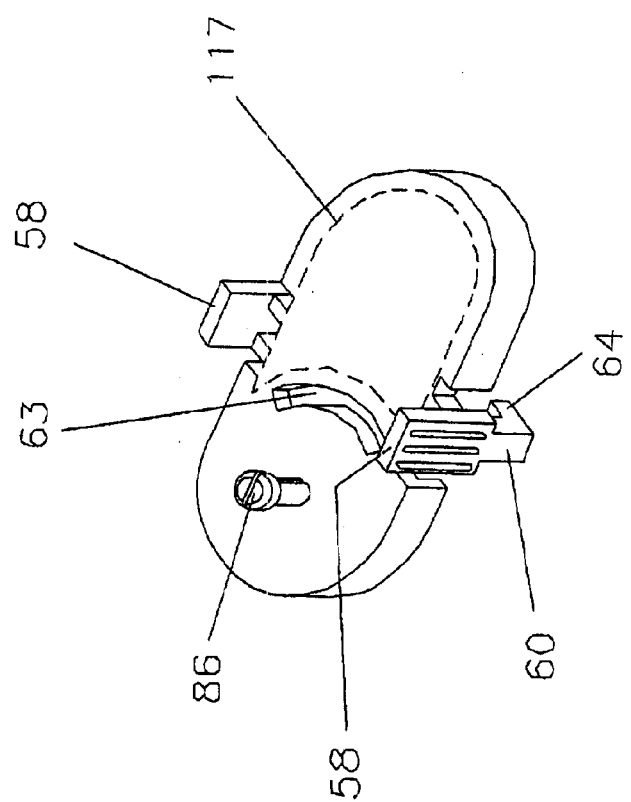
FIG. 5a is a perspective view of a snap-on bristle platform having a post and an area having an array of bristle planting holes (not illustrated).
Figure 9B:
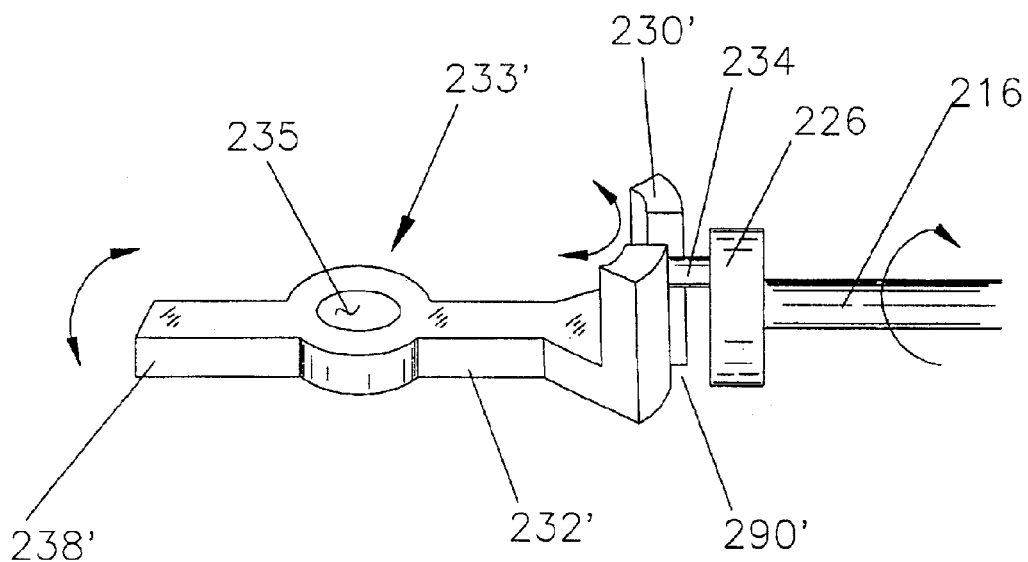
Figure 9A:
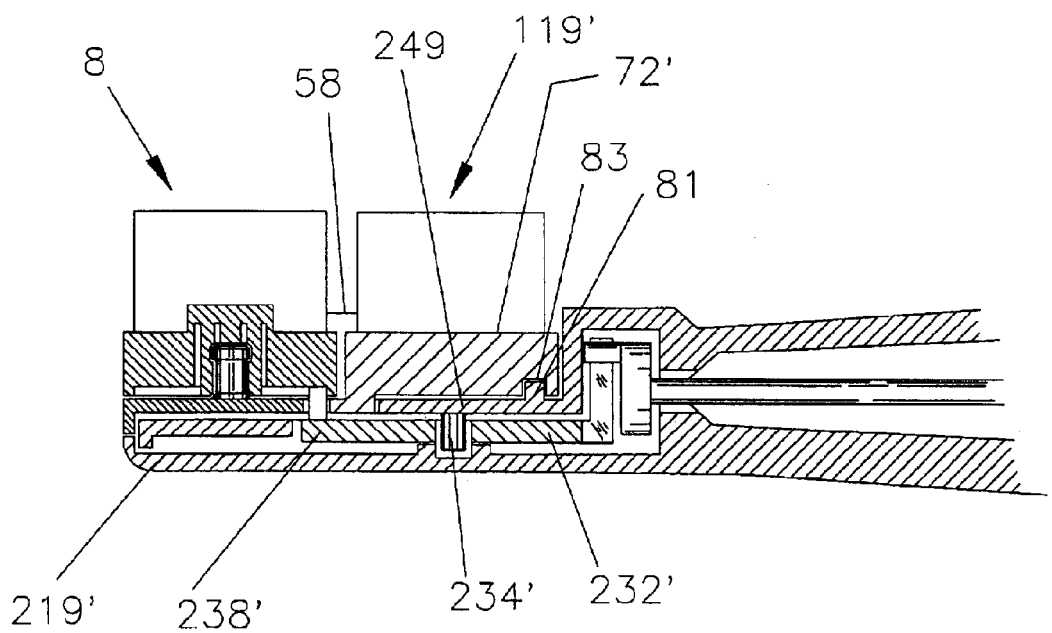
FIG. 9a is a cross section view of the mounting of a replaceable bristle unit on a drive head having an oscillation linkage with a straight lever.

For a replaceable bristle unit using combined rotary and stationary bristle elements as shown in FIGS. 5a and 5b, the elbow-shaped configuration 244 of linkage lever 232 as shown in FIG. 8 is replaced by a straight configuration. FIG. 9a shows the mounting of the replaceable unit of rotary and stationary bristle elements 8 and 119' on drive head 219' having oscillation linkage 233' with straight lever 232' as shown in FIG. 9b. Oscillation linkage 233' having straight lever 232' consists of swing arm 238' at the output end, notch walls 230' at the input end, bushing through hole 235 positioned between the two ends for accommodating stud shaft 234' which extends from the underside of top wall 249 of drive head 219'. Referring to FIG. 9b, the input end has parallel notch walls 230' forming notch 290', which is engaged with offset rod 234 of cam 226 of drive shaft 216. The width of notch 290' is the same as the diameter of offset rod 234. The length of notch walls 230 is sufficient to enable the inner surface of the notch wall to remain in contact with offset rod 234 during a full 360 degree rotation of drive shaft 216. With bushing hole 235 engaged with stud shaft 234' which extends from the inner surface of top 249, straight lever 232' converts the rotation motion of drive shaft 216 to planar oscillation of swing arm 238'. Since stationary bristle element 119' is used, output swing arm 238' of the linkage engages only with the drive notch of the rotary bristle element 8 and causes it to have angular oscillation. Because of the straight arm configuration of the linkage, drive head 219' has lower profile than that using an elbow-shaped oscillation linkage.

Figure 10A:
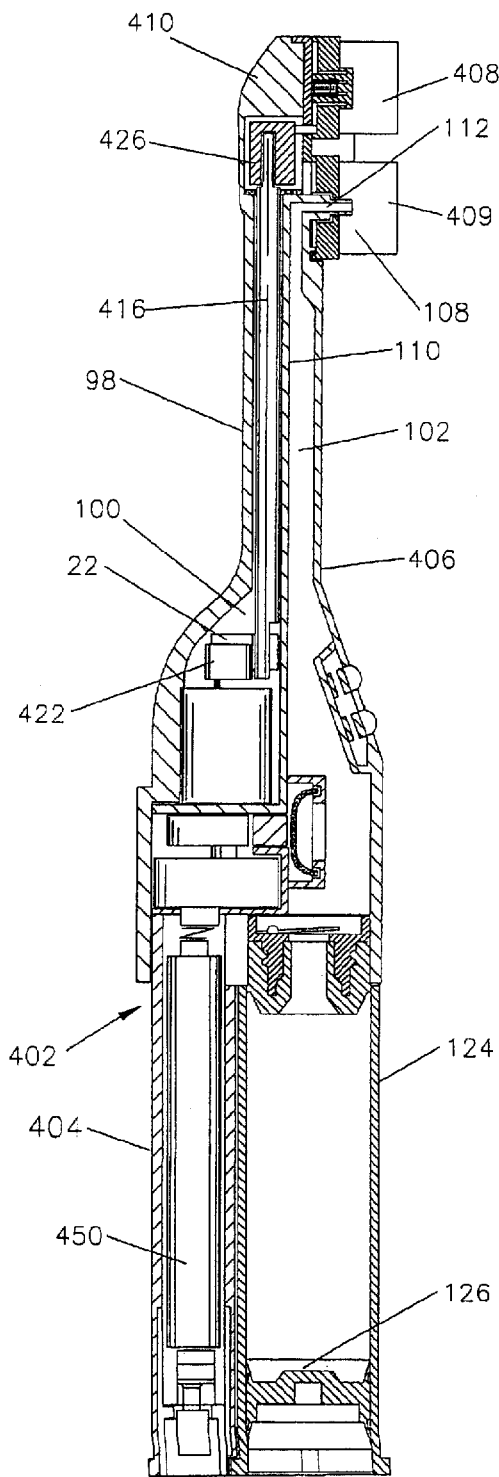
FIG. 10a is a cross section view of a dentifrice dispensing electrical toothbrush with the pumping actuator in the non-dispensing position.
Figure 10B:
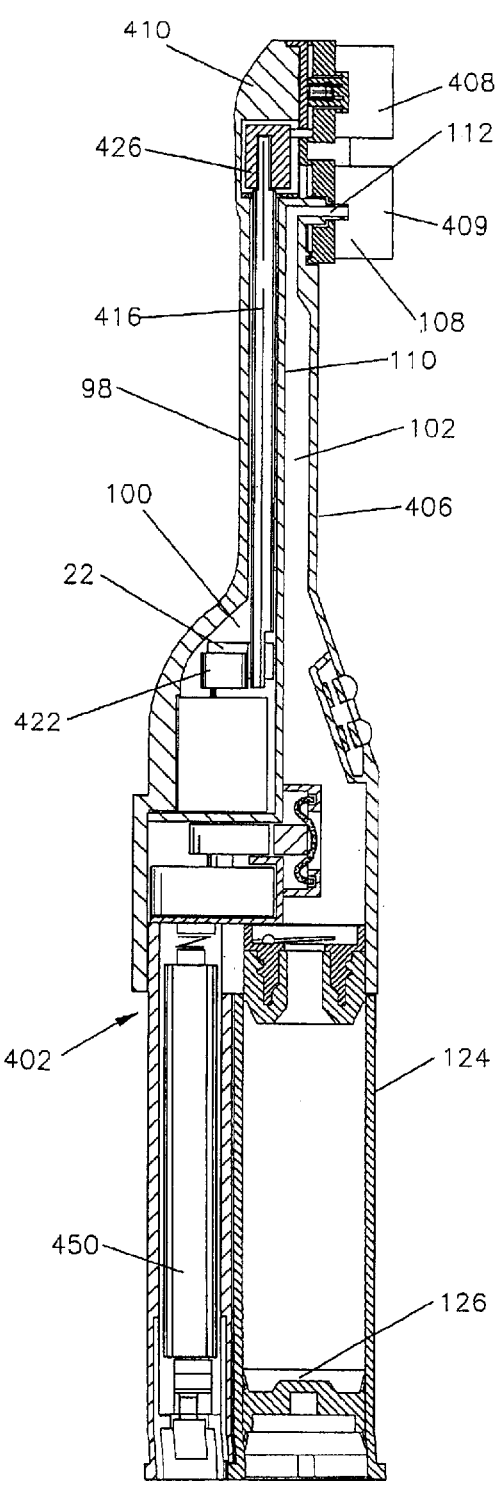
FIG. 10b is a cross section view of a dentifrice dispensing electrical toothbrush with the pumping actuator in the dispensing position.

The replaceable bristle unit structure of the present invention is also applicable to a dentifrice-dispensing toothbrush such as that shown and described in U.S. Pat. No. 5,909,977 by Kuo. A dentifrice-dispensing electrical toothbrush of the present invention integrates a replaceable bristle unit having a spout opening with an electrical means to dispense the dentifrice material stored in the reservoir of the handle to the top of bristles through the spout opening. As shown in FIGS. 10a and 10b, dentifrice-dispensing electrical toothbrush 402 has handle 404, neck 406 and replaceable bristle unit having bristle elements 408 and 409 mounted on drive head 410. Neck 98 has two chambers that are separated by partition 110. Channel 100 contains the drive shaft 416 while flow channel 102 provides the flow path for dentifrice material from the pump chamber 94 to bristle element 409. Similar to FIG. 1a, U-shaped cam 22 is positioned between one end of drive shaft 416 and motor 412. Cap 426 with drive tab 434 is attached to the second end of drive shaft 416. Motor 412 is powered by battery 450 which is stored in handle 404. Dentifrice containing cartridge 124 having follower 126 is detachably mounted in handle 404. Dentifrice material is pumped from pump chamber 94, through channel 102 and spout opening 114, to bristle element 409. The delivery of dentifrice material is achieved using an electrical-mechanical actuator that consists of rotary solenoid 456, cam 454, and plunger 452 for contacting on resilient compressible button 96 as shown in FIG. 10a, which shows these components at the non-dispensing home positions. Upon activating rotary solenoid 456 by pushing on button switch 460 positioned on the external surface 468 of handle 404, cam 454 which is mounted on the shaft of the rotary solenoid 456 rotates 180 degree from the non-dispensing home position to move plunger 452 forward to depress on compressible button 96 to the fully compressed dispensing position. The compression of the resilient compressible button provides the pumping force to push the dentifrice material to the bristle areas through the spout opening. FIG. 10b shows cam 454, plunger 452 and resilient compressible button 96 at the dispensing positions. Then upon the release of button switch 460, through a control circuitry (not shown) rotary solenoid 456 is energized to cause cam 454 to return to the home position, at which point the resiliency of the compressible button 96 not only restores the compressible button to its original position but also causes the plunger to move backward to the home position. During the recovery of the resilient compressible button to its original shape, the vacuum created in chamber causes dentifrice material to flow from cartridge 124 through one way check valve 122 and into chamber 94 to replace the quantity of dentifrice material removed from the pumping force. The flow of dentifrice material from cartridge 124 causes advancement of follower 126 at the base of the cartridge. Repeated actuation of switch button 460 can pump additional dentifrice material to the top of bristle element 409. Although the use of a rotary solenoid is preferred, the actuation of the plunger for compressing on the elastic button can be achieved by linear solenoid or a clutch connected to motor 412.

Also shown in FIG. 10a, while post 106 of rotary bristle element 410 has split walls as described previously, post 108 is hollow and in communication with flow channel 100 and terminates at opening 114 forming spout 115. The outer wall of spout 115 is part of post 108. Platform 121 mounted with bristle elements 8 and 120 as shown in FIG. 11b is detachably secured to drive head 410 as shown in FIG. 11c, which is an enlarged view of the drive head as shown in FIGS. 10a and 10b, by latch arm 60 and rib 64. Referring to FIG. 11a, in addition to an array of tuft holes for stationary bristle element 120, platform 121 has opening 112 which is shaped to mate with hollow post 108. When replaceable bristle unit 401 is mounted on drive head 410, opening 112, spout 115, and channel 102 are aligned to provide a continuous path for dentifrice material to flow from chamber 94 to the bristles of bristle element 120.

When all of the dentifrice material is depleted from cartridge 124, the cartridge is removed from the handle and replaced by a full cartridge. Cartridge 124 is fastened by threads to one way check valve 122 and retained in position by holding arms (not shown) which are part of the outside wall of the handle. The partial exposure of the cartridge facilitates cleaning of the handle wall when the cartridge is replaced. Sealing of spout opening 114 of the dentifrice dispensing electrical toothbrush is similar to that described in U.S. Pat. No. 5,909,977 by Kuo.

The invention has been described in detail with reference to preferred embodiments thereof. However, it is understood that variations and modifications can be effected within the spirit and scope of the invention.

I claim:

1. An electrical toothbrush comprising:
   a. a handle having a motor;
   b. a neck extending from the handle having a drive shaft which has first end and second end with the first end connected to said motor;
   c. a drive head extending from said neck having an oscillation driver attached to the second end of said drive shaft, said drive head has a base having a top and two side walls;
   d. a bristle unit mounted on said drive head having:
      i. a first rotary bristle element comprising a base having a side wall between a top surface and a bottom surface, a pair of notch walls extending from the side wall forming a drive notch, a plurality of bristles attached to the top surface, and a bushing extending from said bottom surface and said drive notch being engaged with said oscillation driver;
      ii. a platform comprising top and bottom surfaces having a first slot therein, a peripheral edge and a first post which extends from the top surface for the mounting and free rotating of said first bristle element with said notch walls positioned and extended beyond said first through slot;
      iii. a retention means for allowing free rotation and preventing separation of first bristle element from first post including;
         a. an annular groove positioned on inner surface of said bushing of first rotary bristle element and said bushing having split bushing walls, the diameter of said annular groove being larger than the inside diameter of said bushing walls;
         b. a protruding annular rim on said first post for engaging with said annlar groove of said bushing of the first rotary bristle element and the diameter of said annular rim is smaller than the diameter of said annular groove but larger than the inside diameter of said bushing walls.

2. The electrical toothbrush of claim 1 wherein the drive shaft has a central longitudinal axis integrally connecting said first end and said second end.

3. The electrical toothbrush of claim 1 wherein a retention means for allowing free rotation and preventing separation of first bristle element from first post including a rib on the inner surface of each said notch wall of first rotary bristle element and the radial distance of the rib being less than the radial distance of the inner edge of said first slot from the axis of said first post.

4. The electrical toothbrush of claim 1 wherein said platform is detachable and having a locking means for fastening said detachable platform on said drive head comprising:
   a. a latch recess on each side wall of said drive head;
   b. two opposing latch arms attached to the peripheral edges of said platform with each latch arm having a rib for detachably engaging with the corresponding latch recesses on said side walls; and
   c. two opposing tabs each attached to the peripheral edge of said platform, wherein inward deflection of the tabs toward each other causes outward deflection of the two opposing latch arms and their disengagement from the latch recesses of said drive head.

5. The electrical toothbrush of claim 1 in which the oscillation driver has a drive tab extending radially outward from the first end of said drive shaft and is mateable with the drive notch in the side wall of said first rotary bristle element.

6. The electrical toothbrush of claim 1 in which the oscillation driver is an oscillation conversion linkage consisting of a pair of notch walls at its input end, a swing arm at its output end and a stud shaft extending from a linkage lever that connects the input end and the output end, said swing arm being engaged with the drive notch of said first bristle element and said input end being in communication with the second end of the drive shaft.

7. The electrical toothbrush of claim 6 in which the notch walls of said input end is engaged with an offset rod of a cam connected to the second end of the drive shaft.

8. The electrical toothbrush of claim 1 wherein said bristle unit includes:
   a. a second rotary bristle element comprising a base having a side wall between a top surface and a bottom surface, a pair of notch walls extending from the side wall forming a drive notch, a plurality of bristles attached to the top surface, and a bushing extending from said bottom surface and said drive notch being engaged with said oscillation driver;
   b. a second post and a second slot positioned in said platform, said second post extends from said top surface for mounting and free rotating of said second bristle element with said notch walls positioned and extended beyond the second slot;
   c. a retention means for allowing free rotation and preventing separation of second bristle element from second post including:
      i. an annular groove positioned on inner surface of said bushing of first rotary bristle element and said bushing having split bushing walls, the diameter of said annular groove being larger than the inside diameter of said bushing walls;
      ii. a protruding annular rim on said first post for engaging with said annular groove of said bushing of the first rotary bristle element and the diameter of said annular rim is smaller than the diameter of said annular groove but larger than the inside diameter of said bushing walls.

9. The electrical toothbrush of claim 8 in which the oscillation driver is an oscillation conversion linkage consisting of a pair of notch walls at its input end, a swing arm at its output end and a stud shaft extending from a linkage lever that connects the input end and the output end, said swing arm being engaged with the drive notches of said first and second bristle elements and said input end being in communication with the second end of the drive shaft.

10. The electrical toothbrush of claim 1 in which the platform includes a stationary bristle element.

11. The electrical toothbrush of claim 10 in which the oscillation driver is an oscillation conversion linkage consisting of a pair of notch walls at its input end, a swing arm at its output end, and a linkage lever that connects the input end and the output end, said swing arm being engaged with the drive notch of said first bristle element and said input end being in communication with the second end of the drive shaft.

12. The electrical toothbrush of claim 1 wherein the bushing of first rotary bristle element has split walls and a gap between said split walls for enabling mounting and free-rotation on said first post and each split wall having an annular groove for engaging with the annular rim of said first post for preventing the detachment of said bushing from said first post.

13. The electrical toothbrush of claim 1 where the first post of said platform has split walls and a gap between said split walls for enabling mounting and free-rotation of said bushing.

14. The electrical toothbrush of claim 1 wherein said bushing of first rotary bristle element and said first post of said platform each having split walls separated by a gap for enabling mounting and free-rotation of said bushing on said first post while each wall of bushing having an annular detent recess for engaging with the annular rim of said first post for preventing the detachment of said bushing from said first post.

15. The electrical toothbrush of claim 14 wherein the orientations of the gaps of the split walls of said bushing of the first rotary bristle element and said first post are not overlapping during the oscillation of the first rotary bristle element.

16. An electrical dentifrice dispensing toothbrush comprising:
   a. a handle having a motor and a reservoir for storing dentifrice material;
   b. a neck extending from the handle having a drive shaft and an flow channel, said drive shaft having a first end and a second end with the first end connected to said motor and said flow channel being in communication with the reservoir;
   c. a drive head extending from said neck having:
      i. a base having a top and two side walls;
      ii. a spout extending from the top and being in communication with the flow channel;
      iii. an oscillation driver attached to the second end of said drive shaft;
   d. a bristle unit mounted on said drive head:
   e. a pumping means including an elastic and compressible button for dispensing dentifrice material from the reservoir to said spout;
   f. an electrical switch;
   g. an actuator in contact with said elastic and compressible button and said actuator is moved to dispensing position and compressing on said elastic and compressible button when the electrical switch is activated and said actuator is moved back to the non-dispensing position when said electrical switch is deactivated.

17. The electrical dentifrice dispensing toothbrush of claim 16 wherein said bristle unit comprising:
   a. a first rotary bristle element comprising a base having a side wall between a top surface and a bottom surface, a pair of notch walls extending from the side wall forming a drive notch, a plurality of bristles attached to the top surface, and a bushing extending from said bottom surface and said drive notch being engaged with said oscillation driver;
   b. a platform being attached to said drive head comprising a ton and bottom surfaces having a first slot therein, a peripheral edge and a first post which extends from the top surface for engaging with the bushing of said first bristle element for free rotating when said notch walls being positioned and extended beyond said first slot;
   c. an opening through the ton and the bottom surfaces of said platform for accommodating said spout;
   d. a second bristle element having a plurality of bristles attached to the top surface of said platform;
   e. a retention means for allowing free rotation and preventing separation of first bristle element from said first post.

18. The dentifrice dispensing electrical toothbrush of claim 16 wherein said retention means including:
   a. an annular groove positioned on inner surface of said bushing of first rotary bristle element and said bushing having split bushing walls, the diameter of said annular groove being larger than the inside diameter of said bushing walls;
   b. a protruding annular rim on said first post for engaging with said annular groove of said bushing of the first rotary bristle element and the diameter of said annular rim is smaller than the diameter of said annular groove but larger than the inside diameter of said bushing walls.

* * * * *